United States Patent
Magdassi et al.

(10) Patent No.: US 6,303,149 B1
(45) Date of Patent: Oct. 16, 2001

(54) METHOD FOR THE PREPARATION OF OXIDE MICROCAPSULES LOADED WITH FUNCTIONAL MOLECULES AND THE PRODUCTS OBTAINED THEREOF

(75) Inventors: Shlomo Magdassi; David Avnir, both of Jerusalem; Alon Seri-Levy, Rehovot; Noa Lapidot, Zion; Claudio Rottman, Jerusalem; Yoram Sorek, Yahus; Orit Gans, Bfraim, all of (IL)

(73) Assignee: Sol-Gel Technologies, Ltd., Tel Aviv (IL)

( * ) Notice: Subject to any disclaimer, the term of this patent is extended or adjusted under 35 U.S.C. 154(b) by 0 days.

(21) Appl. No.: 09/372,176

(22) Filed: Aug. 11, 1999

Related U.S. Application Data

(60) Provisional application No. 60/097,552, filed on Aug. 13, 1998.

(51) Int. Cl.[7] ................. A61K 9/14; A61K 9/50
(52) U.S. Cl. .............. 424/489; 424/59; 424/60; 424/401; 264/4.1; 264/4.3; 514/937; 514/951; 428/402.2
(58) Field of Search .................... 424/489, 490, 424/401, 59, 60; 264/4.1, 4.3; 428/402.2, 402.24

(56) References Cited

U.S. PATENT DOCUMENTS

| | | | | |
|---|---|---|---|---|
| 4,349,456 | * | 9/1982 | Sowman | 252/317 |
| 4,988,744 | * | 1/1991 | Yamamoto | 523/102 |
| 5,292,801 | * | 3/1994 | Avnir et al. | 525/54.1 |
| 5,520,917 | * | 5/1996 | Mizuguchi et al. | 424/401 |
| 5,670,209 | * | 9/1997 | Wycoff | 427/215 |
| 5,895,757 | * | 4/1999 | Pope | 434/176 |

* cited by examiner

*Primary Examiner*—James M. Spear
(74) *Attorney, Agent, or Firm*—Lowe Hautpman Gilman & Berner, LLP

(57) ABSTRACT

The present invention relates to a novel process for preparing sol-gel microcapsules loaded with up to 95% (w/w) functional molecules or substances and to the products obtained by said process. Said process is conducted in two steps: (a) creating an oil-in-water emulsion by emulsification of a water insoluble solution comprising the sol-gel precursors and the molecules to be loaded, in an aqueous solution under appropriate shear forces; (b) mixing and stirring said emulsion with an aqueous solution at a suitably selected pH to obtain loaded sol-gel microcapsules in suspension. The microcapsules so obtained can further be subjected to cycles of isolation and rinsing. Incorporation of the final product, either in the form of a suspension or a powder, in cosmetic formulations affords a transparent cream when applying to skin and has a smooth and pleasant contact.

27 Claims, No Drawings

METHOD FOR THE PREPARATION OF OXIDE MICROCAPSULES LOADED WITH FUNCTIONAL MOLECULES AND THE PRODUCTS OBTAINED THEREOF

This application claims the benefit of Provisional Application No. 60/097,552 filed Aug. 13, 1998.

FIELD OF THE INVENTION

The present invention generally relates to a method for isolating functional molecules or substances in inert matrices. More specifically the present invention relates to a method for the preparation of 0.01–100$\mu$ sol-gel microcapsules loaded with up to 95% functional molecules or substances which can be dissolved in sol-gel precursors wherein the sol-gel precursors can be a metal or a semi-metal alkoxide monomer, or a partially hydrolyzed and partially condensed polymer thereof, or a mixture of any of the above. The present invention also relates to the products obtained by this process. The particle size of the final product can be controlled to the range 0.01–100$\mu$, more preferably 0.1–10$\mu$. Under appropriate choice of the reaction conditions said product is in the form of an aqueous suspension of up to 60% solids, consisting of sphere particles of 0.1–10$\mu$ or in the form of fine powder with a smooth and pleasant texture consisting of sphere particles of 0.1–10$\mu$.

BACKGROUND OF THE INVENTION

The present invention generally relates to a method for preparing sol-gel particles that encase or encapsulate or entrap (hereinafter called loading) functional molecules or substances. The term "functional molecules or substances" in the present invention relates to any molecules or substances that can be used in agriculture and industry.

Isolating functional molecules or substances in inert matrices has many useful benefits and applications where chemical contact between the functional molecules and the immediate environment should be minimized. For example, make-up compositions, such as make-up colors are currently using a very limited number of approved natural pigments and even fewer artificial organic colors. Many dyes and pigments with desired color shades of natural or synthetic origin are not approved for skin contact because their safety for direct skin contact has not been demonstrated. Isolating the colorants in transparent and inert isolating material provides a way to prevent the direct contact between the color molecules and the skin, while retaining (or even enhancing) the color intensity. Another very important application is in sunscreen compositions. The active ingredients in sunscreens have been reported to cause contact dermatitis and may cause photocontact dermatitis. Moreover, the light-excited species of these reagents may undergo photodecomposition reactions resulting in the production of free radicals and reactive oxygen species, which may bear deleterious effects on live tissues. Thus, encapsulating sunscreen active ingredients in a transparent matrix like silica offers a sophisticated way to benefit from the light-absorbing capability of sunscreens, while substantially isolating them and/or their possible photodecomposition products from the live tissues. Another example, from a totally different field, is the encapsulating of food colors either for prolonging the shelf life of food products containing unstable natural colors such as lycopene and carotene or for isolating artificial food colors that have undesirable side effects. Encapsulating food colors of the second type in inert transparent microcapsules provides a way to prevent the digestion of these colorants while maintaining their desired color effect.

Recognizing that metal and semi metal alkoxide monomers (and their partially hydrolyzed and condensed polymers) such as tetramethoxy silane (TMOS), tetraethoxy silane (TEOS), methyl triethoxy silane (MeTEOS) etc. are very good solvents for numerous molecules and substances facilitated the development of this method, which utilizes this solubility to load the dissolved molecules or substances in the hydrolysis-condensation polymer of the monomer solvent. Nonetheless, the present invention may also be used to coat or load particles or substances which can be suspended in the sol-gel precursors.

The current invention reveals how to obtain sol-gel materials containing high loading of active ingredients, up to 95% (w/w). Such high loading is required, for example, in order to obtain high Sun Protection Factor (SPF) values. It also facilitates the entrapment or encapsulation of many other molecules or substances, where the application may demand high loading of the entrapped molecule or substance.

The loaded molecules or substances can be any molecules or substances that are soluble or that can be suspended in the metal or semi-metal alkoxides of choice. Examples for such molecules or substances are: ultra-violet absorbing molecules or reflecting substances used in sunscreens, fragrances, perfume, colors and dyes, food colors and food additives, antioxidants, humidifiers, vitamins, explosives, insecticides, herbicides and fungicides, or biological molecules such as enzymes or antibodies, as well as various drugs, catalysts and reagents.

The current invention further teaches how to obtain controlled physical form of the product. In a preferred embodiment, it teaches how to obtain capsules and microcapsules of sol-gel derived material, containing the loaded molecule or substance, with a smooth and pleasant contact.

The product by process may accordingly vary for human or non-human applications, as the obtained aqueous suspension and the obtained dry powder may be easily incorporated in various carriers, such as creams and lotions, processed food, sprays, paints, lacquers, coatings, plastics and detergents.

SUMMARY OF THE INVENTION

The present invention relates to a novel process for preparing sol-gel particles loaded with up to 95% (w/w) functional molecules and to the products obtained by said process. Said process is conducted in two steps: (a) creating an oil-in-water emulsion by emulsification of a water insoluble solution comprising the sol-gel precursors and the molecules to be loaded, in an aqueous solution under appropriate shear forces; (b) mixing and stirring the said emulsion with an aqueous solution at a suitably selected pH to obtain loaded sol-gel particles of 0.01–100$\mu$. (In the present invention the term "mixing" also relates to dropwise addition of one solution to the other, by pouring one solution to the other, or any other method of combining the two solutions together).

After an appropriate reaction time, during which the mixture may be heated or cooled, subject to vacuum, changes in pH and optionally an aging period, the resulting particles may be isolated and rinsed through cycles of centrifuge or filtration and re-suspension in deionized water or by any other means known in the art.

The water insoluble solution (of step a) and the aqueous solutions (of steps a and b and in the optional further rinses) may contain various surfactants and any other additives for improving the process and/or the product.

By selecting the appropriate reaction conditions, the particle size of the final product can be controlled to be in the range from 0.01 to 100µ and the leaching degree of the loaded molecule into cosmetic oils or into the surfactant-containing aqueous solution can be minimized.

The sol-gel precursors can be a metal or a semi-metal alkoxide monomers, or a partially hydrolyzed and partially condensed polymer thereof, or a mixture thereof. The functional molecules and substances can be any molecules and substances that can be used in agriculture and industry.

In a preferred embodiment of the present invention, under appropriate choice of the reaction conditions, said product is in the form of a suspension containing about 1 to 60% solids consisting of sphere particles of 0.1–10µ.

Said suspension may be stabilized with the aid of suitable additives such as non-ionic, cationic or anionic polymers, or any other suspension aid known to the skilled artisan in this field This suspension shows extremely low leaching of the encapsulated material into surfactants solution in water, or into cosmetic oils. Incorporation of this aqueous suspension in a cosmetic formulation affords a transparent cream when applying to skin and has a smooth and pleasant contact.

In another preferred embodiment of the present invention, under appropriate choice of the reaction conditions said product is in the form of a fine powder with a smooth and pleasant texture consisting of sphere particles of 0.1–10µ. Dispersion of this powder in a cosmetic formulation affords a transparent cream when applying to skin and has a smooth and pleasant contact.

DETAILED DESCRIPTION OF THE INVENTION

The present invention relates to a process for the preparation of sol-gel microcapsules of 0.01–100µ, loaded with functional molecules or substances.

The process is based on the preparation of an oil-in-water emulsion of the hydrophobic solution that comprises the sol-gel precursors and the molecules or substances to be loaded, in aqueous solution and then mixing said emulsion with another aqueous solution to accelerate the condensation-polymerization reaction.

The polymerization progresses through condensation-polymerization of at least one monomer selected from metal alkoxides, semi-metal alkoxides, metal esters, semi-metal esters and from monomers of the formula $M(R)_n(P)_m$, wherein M is a metallic or semi metallic element, R is a hydrolyzable substituent, n is an integer from 2 to 6, P is a non polymerizable substituent and m is and integer from 0 to 6.

In a preferred embodiment of this invention, the sol-gel precursors are silicon alkoxide monomers, or silicon ester monomers, or monomers of the formula $Si(R)_n(P)_m$, where R is a hydrolyzable substituent, n is an integer from 2 to 4, P is a non polymerizable substituent and m is and integer from 0 to 4, or partially hydrolyzed and partially condensed polymer thereof, or any mixture thereof.

In another preferred embodiment of the present invention, the sol-gel precursors are titanium alkoxide monomers, or titanium ester monomers, or monomers of the formula $Ti(R)_n(P)_m$, where R is a hydrolyzable substituent, n is an integer from 2 to 6, P is a non polymerizable substituent and m is and integer from 0 to 6, or partially hydrolyzed and partially condensed polymer thereof, or any mixture thereof.

In another preferred embodiment of the present invention, the sol-gel precursors are zinc or zirconium alkoxide monomers, or zinc or zirconium ester monomers, or monomers of the formula $Zn(R)_n(P)_m$ or $Zr(R)_n(P)_m$, where R is a hydrolyzable substituent, n is an integer from 2 to 6, P is a non polymerizable substituent and m is and integer from 0 to 6, or partially hydrolyzed and partially condensed polymer thereof, or any mixture thereof.

In yet another preferred embodiment of this invention, several sol-gel precursor are used together in a mixture, including mixtures of several metals or semi metal compounds, to afford a sol-gel material which is a composite containing different metal and/or semi metal elements in the final product.

The loaded molecules or substances may be any molecules or substances that are soluble or that can be suspended in the metal or in the semi metal alkoxides of choice. Examples for molecules or substances that can be loaded include sunscreens, fragrances, perfume, colors and dyes, food colors and food additives, antioxidants, humidifiers, vitamins, explosives, insecticides, herbicides and fungicides, or biological molecules such as enzymes or antibodies, as well as various drugs, catalysts and reagents. The product by process may accordingly vary for human or non-human applications, as the obtained powder may be easily incorporated in various carriers, e.g. creams and lotions, processed food, sprays, paints, lacquers, coatings, plastics, detergents etc.

Said process is conducted by the following steps:

(a) A solution consisting of the water insoluble metal alkoxides with or without a co-solvent and/or surfactant and the molecules to be entrapped is emulsified in an aqueous solution, that may contain various surfactants, i.e. cationic, anionic or non-ionic surfactants, which are utilized to assist in stabilizing the emulsions. This emulsion is created under appropriate shear forces, utilizing an apparatus such as a homogenizer, a high pressure homogenizer or a sonicator. The oil phase of the emulsion may optionally contain additives for improving the process and/or for obtaining an improved product. Examples for such additives are viscosity modifying reagents (i.e., thickeners), acids or bases that dissolve in the sol-gel precursor of choice and assist in catalyzing the hydrolysis-condensation polymerization reaction, surfactants and others.

(b) The emulsion obtained by step (a) is mixed with an aqueous solution at a suitably selected pH (basic, neutral or acidic), which may also contain additional surfactants. The aqueous solution may also contain additives for improving the process and/or for obtaining an improved product such as glass water. The reaction mixture may be heated or cooled, subject to vacuum, or pressure, or kept under inert gas atmosphere, subject to changes in pH and with an optional further aging period.

The resulting particles can be isolated and rinsed through cycles of centrifuge or filtration and re-suspension in deionized water or by dialysis or by any other technique known in the art.

The final product may be used in a dispersion form, after re-suspension in water with optional addition of suitable additives such as non-ionic, cationic or anionic polymers, or any other suspension aid known to the skilled artisan in this field. This dispersion shows extremely low leaching of the encapsulated material into surfactants solution in water, or into cosmetic oils.

The final product may also be used in a powder form, after removal of the water by appropriate means (drying, lyophilization, etc.) with optional addition of reconstitution additives such as non-ionic, cationic or anionic surfactants or polymers.

The loading of the loaded molecules or substances in the oxide carrier may be from zero up to 95% weight of the solid. The loading of the loaded molecules or substances in the final aqueous dispersion may be up to 50% wt/wt of the aqueous suspension.

The particle size of the final product can be controlled to the range 0.01–100$\mu$, more preferably 0.1–10$\mu$. The particles obtained by the present process can sustain high shear forces such as those present in a homogeizer or a sonicator without change in their encapsulation properties or in particle size distribution. The particles can also sustain increased temperatures up to 80° C. for 2 hours, without any such change.

The product by process may be designed to hold and/or isolate the entrapped molecules within the sol-gel matrix, or to act as a matrix for controlled or sustained release of the loaded molecules.

EXAMPLES

The following examples clarify and demonstrate the present invention. They are not under any circumstances exclusive and do not intend to limit the scope of the present invention.

Background to Examples 1–7

As was mentioned in the background, the case of encapsulated sunscreen reagents is of a special importance. Sunscreen products are widely used all over the world by all ages and gender, however, not only that the active ingredients in these products may cause contact dermatitis, but also the light-excited species of these reagents may cause photocontact dermatitis. Thus, encapsulating sunscreen active ingredients in a transparent matrix like silica offers a sophisticated way to benefit from the light-absorbing capability of sunscreens, while substantially isolating them and/or their possible photodecomposition products from the live tissues.

Example 1
Octylmethoxy Cinnamate (OMC) in TEOS (Tetraethoxy Silane)

Octylmethoxy cinnamate (OMC), a widely used sunscreen has been encapsulated in a silica matrix by the following procedure:

11 g OMC was dissolved in 33 g TEOS. The organic phase was emulsified in 200 g of aqueous solution containing 1% cetyltrimethyl ammonium chloride (CTAC) under high shear forces using an Ultra-Turrax T-25 basic with S 25 KR-18G dispersing tool (IKA) at 19,000 rpm. The vessel walls were cooled by immersion in an ice-water bath during the homogenizing process. This emulsion was then poured into an IKA LR-A 1000 Laboratory reactor, equipped with Eurostar Power control-visc P4 stirrer, containing 200 g NaOH aqueous solution at pH 11.3. The solution is stirred at 400 rpm while the emulsion is added, then the stirring rate lowered to 200 rpm. The emulsion is stirred at room temperature for 24 hours, followed by stirring at 50° C. for 3 hours. The obtained powder is washed with deionized water and freeze dried.

The product of this process consists of 68% (w/w) OMC, encapsulated in silica spheres of 0.5 to 3.5 micron.

Formulation of this powder in Formula A (Table 1) affords a transparent cream when applying to skin and has a smooth and pleasant contact, with an in-vitro SPF value of 13.3.

Example 2
Benzophenone-3 (BP) and OMC in TEOS 3 g benzophenone-3, an UV-B as well as UV-A sunscreen agent, was dissolved in 8 g OMC. The obtained mixture was dissolved in 33 g TEOS and the organic phase was emulsified under high shear forces (same as described in Example 1) in 200 g aqueous solution containing 1% ethoxylated sorbitan monooleate (Tween-80, ICI). The obtained emulsion was then poured into the reactor (same as above) containing 200 g of 0.1 triethanolamine and 4M NaOH (pH 11.4). The emulsion is stirred at room temperature for 24 hours, followed by stirring at 50° C. for 3 hours. The obtained powder is washed with water and freeze dried to give a fine silica powder with a slight yellow color.

The spectrum of this product when suspended a neutral cosmetic cream (w/o lotion, a commercial source) affords a cream with a broad absorption in the UV, as expected from a mixture of the two sunscreens used. The cream looks transparent when applied on the skin.

Example 3
BP and OMC in TEOS 2.5 g BP was dissolved in 14 g OMC. The obtained mixture was dissolved in TEOS and the organic phase was treated in a similar manner to that described in Example 1. Nitrogen gas was bubbled through the solution during the reaction course. The obtained powder was washed with water and freeze dried to give a fine silica powder. The product of this process consists of 55% (w/w) OMC and 10% (w/w) BP, encapsulated in silica spheres of 0.5 to 3$\mu$.

Formulation of this powder in Formula B (Table 1) affords a transparent cream when applying to skin and has a smooth and pleasant contact, with an in vitro SPF value of 28.2, with a UVA factor of 5.7.

Example 4
Butylmethoxydibenzoyl Methane (BMDBM) in Homomenthyl Salicylate (HMS)

3.3 g BMDBM, a UVA sunscreen agent, was dissolved in 13.2 g HMS, a UVB absorber. The obtained mixture was dissolved in TEOS and the organic phase was treated in a similar manner to that described above. The reaction mixture was allowed to stand for another 48 h before isolating the product. The product was precipitated with a centrifuge and rinsed by re-suspension in deionized water. The final product was suspended in a 1% polyvinyl pyrrolidono (PVP K30, ISP) to afford a stable dispersion containing 10.5% BMDBM and 20.7% HMS. The particle size was 1–5$\mu$.

Formulation of this powder in Formula C (Table 1) affords a transparent cream when applying to skin and has a smooth and pleasant contact, with an in vitro SPF value of 5.9, with a UVA factor of 5.0.

Example 5
OMC in Poly(Diethoxysiloxane)

2.75 g OMC was dissolved in 8.25 g poly (diethoxysiloxane) (ABCR PSI-021 or PSI-023). The organic phase was treated in a similar manner to that described in example 1. The obtained powder is washed with water and freeze dried to give a fine silica powder. The product of this process using PSI-021 consists of 25% (w/w) OMC encapsulated in silica spheres of 0.5 to 5$\mu$. The product of this process using PSI-023 consists of 35% (w/w) OMC encapsulated in silica spheres of 0.5 to 10$\mu$.

Example 6
OMC in Methyltriethoxysilane 1.1 g OMC was dissolved in 9.9 g methyltriethoxysilane. A similar procedure is described in Example 5 was followed.

The obtained powder was washed with water and freeze dried to give a fine silica powder.

Example 7
OMC in TEOS

OMC/silica particles were prepared in a similar manner to that described in example 1. The final product was suspended in a 1% polyvinyl pyrrolidone (PVP K30, ISP) to afford a stable dispersion containing 34% OMC in the suspension.

Leaching-out test: In order to test the encapsulating properties of the silica particles a leaching-out test was developed. It was found that vigorous shaking of the suspension in 3% polyoxyethylene (20) sorbitan monostearate (Tween 60) solution in water at room temperature, followed by filtration of the silica particles ($0.2\mu$ cut off filter), and spectral analysis of the free OMC in the solution, gives a linear response at the range 0.1–0.5% (w/w) OMC in the surfactant solution. This surfactant is commonly used in cosmetic formulations. The ability of this solution to solubilize OMC in water was confirmed by testing this procedure on free OMC. The leaching-out rate measured as described here for the silica suspension was less than 1%. No significant change in the leaching rate under the same conditions is observed after homogenization of the suspension with an Ultra-Turrax T-25 basic with S 25 KR-18G dispersing tool (IKA) at 11,000 rpm for 5 minutes.

The following examples clarify and demonstrate the invention in applications other than sunscreen active ingredients.

Example 8
β-Carotene in TEOS

β-Carotene, a widely used natural food colorant, has been encapsulated in a silica matrix by the following procedure:

1.2 g β-Carotene was dissolved in 31.8 g TEOS. The procedure was similar to that described above. The obtained product was washed, isolated and freeze dried to give a strong orange colored fine silica powder. The powder can be easily suspended in hydrophilic phases like water, milk, yogurt, etc, affording a colored suspension. Heating of an aqueous suspension containing the encapsulated carotene to 90° C. for 10 minutes does not alter the color of the solution.

TABLE 1

SPF values of formulations containing sunscreen-loaded oxide particles obtained by the process of the present invention (concentrations are given in wt. %).

| | A (Example 1) | B (Example 3) | C (Example 4) |
|---|---|---|---|
| water | 77.7 | 76.0 | 41.6 |
| Squalane | | | 5.0 |
| Squalene | 5.0 | 5.0 | |
| Glyceryl stearate & PEG-100 stearate | 5.0 | 5.0 | 5.0 |
| Cetyl alcohol | 2.0 | 1.0 | 2.5 |
| Methyl parabene | 0.1 | 0.2 | 0.2 |
| Propyl parabene | 0.1 | 0.1 | 0.1 |
| Na$_2$EDTA | | | 0.05 |
| Imidazolidinyl urea | | | 0.5 |
| Methylchloroisothiazolinone & Methylchlorothiazolinone & Benzyl alcohol | | | 0.05 |
| Silicapowder | 10.0 | 15.0 | |
| Silica suspension | | | 48.4 |
| OMC in final formulation | 6.8 | 8.25 | |
| BP in final formulation | | 1.5 | |
| BMDBM in final formulation | | | 5.1 |

TABLE 1-continued

SPF values of formulations containing sunscreen-loaded oxide particles obtained by the process of the present invention (concentrations are given in wt. %).

| | A (Example 1) | B (Example 3) | C (Example 4) |
|---|---|---|---|
| HMS in final formulation | | | 10 |
| In vitro SPF | 13.3 | 28.8 (5.7UVA factor) | 5.9 (5.0UVA factor) |

Example 9
Lycopene in TEOS

Lycopene, a widely used natural food colorant, has been encapsulated in a silica matrix by the following procedure:

1.2 g Lycopene (extract from tomatoes) was dissolved in 31.8 g TEOS. The procedure was similar to that described above. The obtained product was washed, isolated and freeze dried to give a bright red colored fine silica powder. The powder can be easily suspended in hydrophilic phases like water, milk, yogurt, etc, affording a colored suspension.

Example 10
Pyrinex in TEOS

O,O-diethyl O-3,5,6,-trichloro-2-pyridyl phosphorothioate (Pyrinex, Machteshim-Agan), a widely used pesticide, has been encapsulated in a silica matrix by the following procedure:

16.5 g Pyrinex was dissolved in 49.5 g TEOS. The procedure was similar to that described above. The obtained product was washed, re-suspended in water or isolated and freeze dried to give a fine silica powder.

The particle size distribution of the product, as measured in a 1% sodium dodecyl sulfate aqueous solution, was between 1 to 15 microns.

What is claimed is:

1. A process for preparing sol-gel microcapsules loaded with up to 95% (w/w) functional molecules, comprising the steps of:
    a) emulsifying a nonaqueous, water insoluble solution, comprising sol-gel precursors and the functional molecules to be loaded, in an aqueous solution, under shear forces and with surfactants;
    b) mixing and stirring the emulsion obtained in step (a) with an acidic, neutral or basic aqueous solution to obtain loaded sol-gel microcapsules in a suspension.

2. A process according to claim 1 wherein the pH of the aqueous solution of step (b) is in the range of 8–13.

3. A process according to claim 1 wherein the mixture of step (b) is heated or cooled, subject to vacuum or pressure, or kept under inert gas atmosphere, subject to changes in pH and with an optional aging period of up to 14 days.

4. A process according to claim 1 wherein the hydrophobic solution in step (a) and the aqueous solution in step (b) contain additional surfactants or any additives to improve the product.

5. A process according to claim 1, comprising the further step of isolating and rinsing the microcapsules through cycles of separation by centrifuge or by filtration and re-suspension in water, or by evaporation and re-suspension in water or by dialysis.

6. A process according to claim 5 wherein the suspension so obtained is stabilized by adding additives selected from the group consisting of non-ionic, cationic and anionic polymers.

7. A process according to claim 5 further comprising the step of removing the water to obtain the final product in a powder form.

8. A process according to claim 7 further comprising adding reconstitution additives selected from the group consisting of non-ionic, cationic and anionic surfactants or polymers.

9. A process according to claim 1 wherein the sol-gel precursors are metal or semi-metal alkoxide monomers, or metal ester monomers, or semi-metal ester monomers or monomers of the formula $M(R)_n(P)_m$, wherein M is a metallic or semi metallic element, R is a hydrolyzable substituent, n is an integer from 2 to 6, P is a non polymerizable substituent and m is an integer from 0 to 6, or partially hydrolyzed and partially condensed polymer thereof, or any mixture thereof.

10. A process according to claim 1 wherein the sol-gel precursors are silicon alkoxide monomers, or silicon ester monomers, or monomers of the formula $Si(R)_n(P)_m$, where R is a hydrolyzable substituent, n is an integer from 2 to 4, P is a non polymerizable substituent and m is an integer from 0 to 4, or partially hydrolyzed and partially condensed polymer thereof, or any mixture thereof.

11. A process according to claim 1 wherein the sol-gel precursors are titanium alkoxide monomers, or titanium ester monomers, or monomers of the formula $Ti(R)_n(P)_m$, where R is a hydrolyzable substituent, n is an integer from 2 to 6, P is a non polymerizable substituent and m is an integer from 0 to 6, or partially hydrolyzed and partially condensed polymer thereof, or any mixture thereof.

12. A process according to claim 1 wherein the sol-gel precursors are zinc or zirconium alkoxide monomers, or zinc or zirconium ester monomers, or monomers of the formula $Zn(R)_n(P)_m$ or $Zr(R)_n(P)_m$, where R is a hydrolyzable substituent, n is an integer from 2 to 6, P is a non polymerizable substituent and m is an integer from 0 to 6, or partially hydrolyzed and partially condensed polymer thereof, or any mixture thereof.

13. A process according to claim 1 wherein several sol-gel precursor are used together in a mixture, including a mixture of several metals or semi metal compounds, to afford a sol-gel material which is a composite containing different metal and/or semi metal elements in the final product.

14. A process according to claim 1 wherein the surface charge of the products is modified by adding anionic or cationic surfactants or polymers during any step of the process.

15. A process according to claim 1 wherein the functional molecules are ultra-violet absorbing molecules or ultra-violet reflecting substances to be used in sunscreens.

16. A process for preparing sol-gel microcapsules loaded with up to 95% (w/w) functional molecules, comprising the steps of:
a) emulsifying a nonaqueous, water insoluble solution, comprising sol-gel precursors and the functional molecules to be loaded, in an aqueous solution, under shear forces and with surfactants;
b) mixing and stirring the emulsion obtained in step (a) with an acidic, neutral or basic aqueous solution to obtain loaded sol-gel microcapsules in a suspension, wherein the functional molecules are ultra-violet absorbing molecules or ultra-violet reflecting substances to be used in sunscreens, wherein the ultra-violet absorbing molecules are selected from the group consisting of 2-ethylhexyl p-methoxycinnamate, p-aminobenzoic acid, 2-ethylhexyl N,N-dimethyl-p-aminobenzoate, 2-cyano-3,3-diphenylacrylic acid 2-ethylhexyl ester (octocrylene), oxybenzone, 2-phenylbenzimidizole-5-sulfonic acid, homomenthyl salicylate, octyl salycilate, 4,4'-methoxy-t-butyldibenzoylmethane, 4-isopropyl dibenzoylmethane, 3-(4-methylbenzyledene) camphor, 3-benzylidene camphor, triethanolamine salicylate, 4-N,N-(2-ethylhexyl)methyl aminobenzoic acid ester of 2,4-dihydroxybenzophenone, 4-N,N-(2-ethylhexyl) methyl aminobenzoic acid ester of 4-hydroxydibenzoylmethane, 4-N,N-(2-ethylhexyl) methyl-aminobenzoic acid ester of 2-hydroxy-4-(2-hydroxyethoxy)-benzophenone, 4-N,N-(2-ethylhexyl) methyl aminobenzoic acid ester of 4-(2-hydroxyethoxy)dibenzoylmethane and a mixture thereof.

17. A process according to claim 1 wherein the functional molecules or substances are selected from the group consisting of fragrances, perfume, colors and dyes, food colors and food additives, antioxidants, humidifiers, vitamins, explosives, insecticides, herbicides and fungicides, or biological molecules selected from the group consisting of enzymes and antibodies, and drugs, catalysts and reagents.

18. A process according to claim 1 wherein the functional molecules are selected from the group consisting of natural food colors, synthetic food colors, and food additives used in food products or oral drugs.

19. A process according to claim 1 wherein the functional molecules are natural food colours or synthetic food colours used in cosmetic colours and skin applications.

20. A process according to claim 1 wherein the functional molecules are selected from the group consisting of insecticides, herbicides and fungicides used in agriculture or industry.

21. The products obtained by the process according to claim 1.

22. The products obtained by the process according to claim 1 in a suspension form.

23. The products obtained by the process according to claim 1 in a powder form.

24. Products according to claim 21 wherein the powder particles or the suspended particles are of 0.01–100$\mu$.

25. Products according to claim 21 wherein the powder or the suspension consists of 0.1–10$\mu$ spherical particles, has smooth texture, and is transparent when suspended in cosmetic or skin care formulations and applied to skin.

26. Products according to claim 21 wherein the leaching of the loaded molecules into cosmetic oils or into a surfactant-containing aqueous solution is less than 5% after vigorous shaking.

27. Products according to claim 26 wherein the leaching of the loaded molecules into cosmetic oils or into a surfactant-containing aqueous solution is less than 2% after vigorous shaking.

* * * * *

UNITED STATES PATENT AND TRADEMARK OFFICE
CERTIFICATE OF CORRECTION

PATENT NO. : 6,303,149 B1
DATED : April 22, 2002
INVENTOR(S) : Shlomo Magdassi et al.

It is certified that error appears in the above-identified patent and that said Letters Patent is hereby corrected as shown below:

Column 1,
Line 10, please replace in it's entirety the paragraph beginning with the following:
-- The present invention generally relates to a method for isolating functional molecules or substances in inert matrices. More specifically the present invention relates to a method for the preparation of 0.01-100u sol-gel microcapsules loaded with up to 95% functional molecules or substances which can be dissolved in sol-gel precursors wherein the sol-gel precursors can be a metal or a semi-metal alkoxide monomer, or a partially hydrolyzed and partially condensed polymer thereof, or a mixture of any of the above. The present invention also relates to the products obtained by this process. The particle size of the final product can be controlled to the range 0.01-100u, more preferably 0.1-10u. Under appropriate choice of the reaction conditions said product is in the form of an aqueous suspension of up to 60% solids, consisting of sphere particles of 0.1-10u or in the form of a fine powder with a smooth and pleasant texture consisting of sphere particles of 0.1-10u. --
Line 35, please replace in its entirety the paragraph beginning with the following:
   -- Isolating functional molecules or substances in inert matrices has many useful benefits and applications where chemical contact between the functional molecules and the immediate environment should be minimized. For example, make-up compositions, such as make-up colors are currently using a very limited number of approved natural pigments and even fewer artificial organic colors. Many dyes and pigments with desired color shades of natural or synthetic origin are not approved for skin contact because their safety for direct skin contact has not been demonstrated. Isolating the colorants in transparent and inert isolating material provides a way to prevent the direct contact between the color molecules and the skin, while retaining (or even enhancing) the color intensity. Another very important application is in sunscreen compositions. The active ingredients in sunscreens have been reported to cause contact dermatitis and may cause photocontact dermatitis. Moreover, the light- excited species of these reagents may undergo photodecomposition reactions resulting in the production of free radicals and reactive oxygen species, which may bear deleterious effects on live tissues. Thus, encapsulating sunscreen active ingredients in a transparent matrix like silica offers a sophisticated way to benefit from the light-absorbing capability of sunscreens, while substantially isolating them and/or their possible photodecomposition products from the live tissues. Another example, from a totally different field, is the encapsulation of food colors either for prolonging the shelf life of food products containing unstable natural colors such as lycopene and carotene or for isolating artificial food colors that have undesirable side effects. Encapsulating food colors of the second type in inert transparent microcapsules provides a way to prevent the digestion of these colorants while maintaining their desired color effect. --

UNITED STATES PATENT AND TRADEMARK OFFICE
CERTIFICATE OF CORRECTION

PATENT NO. : 6,303,149 B1
DATED : April 22, 2002
INVENTOR(S) : Shlomo Magdassi et al.

It is certified that error appears in the above-identified patent and that said Letters Patent is hereby corrected as shown below:

Column 2,
Line 36, please replace in its entirety the paragraph beginning with the following:
  -- The product by-process may accordingly vary for human or non-human applications, as the obtained aqueous suspension and the obtained dry powder may be easily incorporated in various carriers, such as creams and lotions, processed food, sprays, paints, lacquers, coatings, plastics and detergents. --
Line 20, please replace in its entirety the paragraph beginning with the following:
  -- The loaded molecules or substances can be any molecules or substances that are soluble or that can be suspended in the metal or semi-metal alkoxides of choice. Examples for such molecules or substances are: ultra-violet absorbing molecules or reflecting substances used in sunscreens, fragrances, perfumes, colors and dyes, food colors and food additives, antioxidants, humidifiers, vitamins, explosives, insecticides, herbicides and fungicides, or biological molecules such as enzymes or antibodies, as well as various drugs, catalysts and reagents. --

Column 3,
Line 6, please replace in its entirety the paragraph beginning with the following:
  -- The sol-gel precursors can be metal or semi-metal alkoxide monomers, or a partially hydrolyzed and partially condensed polymer thereof, or a mixture thereof. The functional molecules and substances can be any molecules and substances that can be used in agriculture and industry. --
Line 15, please replace in its entirety the paragraph beginning with the following:
  -- Said suspension may be stabilized with the aid of suitable additives such as non-ionic, cationic or anionic polymers, or any other suspension aid known to the skilled artisan in this field. This suspension shows extremely low leaching of the encapsulated material into surfactants solution in water, or into cosmetic oils. Incorporation of this aqueous suspension in a cosmetic formulation affords a transparent cream when applying to skin and has a smooth and pleasant contact. --

Column 4,
Line 7, please replace in its entirety the paragraph beginning with the following:
  -- In yet another preferred embodiment of this invention, several sol-gel precursors are used together in a mixture, including mixtures of several metals or semi-metal compounds, to afford a sol-gel material which is a composite containing different metal and /or semi-metal elements in the final product. --

UNITED STATES PATENT AND TRADEMARK OFFICE
CERTIFICATE OF CORRECTION

PATENT NO. : 6,303,149 B1
DATED : April 22, 2002
INVENTOR(S) : Shlomo Magdassi et al.

It is certified that error appears in the above-identified patent and that said Letters Patent is hereby corrected as shown below:

Column 4, cont.
Line 27, please replace in its entirety the paragraph beginning with the following:
   -- Said process is conducted by the following steps:
   (a) A solution consisting of the water insoluble metal alkoxides with or without a c-solvent and/or surfactant and the molecules to be entrapped are emulsified in an aqueous solution, that may contain various surfactants, i.e. cationic, anionic or non-ionic surfactant which are utilized to assist in stabilizing the emulsions. This emulsion is created under appropriate shear forces, utilizing an apparatus such as a homogenizer, a high pressure homogenizer or a sonicator. The oil phase of the emulsion may optionally contain additives for improving the process and/or for obtaining an improved product. Examples for such additives are viscosity modifying reagents (i..e., thickeners), acid or based that dissolve in the sol-gel precursor of choice and assist in catalyzing the hydrolysis-condensation polymerization reaction, surfactants and others. --

Column 5,
Line 48, please replace in its entirety the paragraph beginning with the following:
   -- 11 g OMC was dissolved in 33 g TEOS. The organic phase was emulsified in 200 g of aqueous solution containing 1% cetyltrimethyl ammonium chloride (CTAC) under high shear forces using an Ultra-Turrax T-25 basic with S 25 KR-18G dispersing tool (IKA) at 19,000 rpm. The vessel walls were cooled by immersion in an ice-water bath during the homogenizing process. This emulsion was then poured into an IKA LR-A 1000 Laboratory reactor, equipped with Eurostar Power control-visc P4 stirrer, containing 200 g NaOH aqueous solution at pH 11.3. The solution is stirred at 400 rpm while the emulsion is added, then the stirring rate is lowered to 200 rpm. The emulsion is stirred at room temperature for 24 hours, followed by stirring at 50 C, for 3 hours. The obtained powder is washed with deionized water and freeze dried. --

Column 6,
Line 3, please replace in its entirety the paragraph beginning with the following:
   -- 3 g benzophenone-3, a UV-B as well as UV-A sunscreen agent, was dissolved in 8 g OMC. The obtained mixture was dissolved in 33 g TEOS and the organic phase was emulsified under high shear force (same as described in Example 1) in 200 g aqueous solution containing 1% ethoxylated sorbitian monooleate (Tween-80, ICI). The obtained emulsion was then poured into the reactor (same as above) containing 200 g of 0.1 triethanolamine and 4M NaOH (pH 11.4). Tkhe emulsion is stirred at room temperature for 24 hours, followed by stirring at 50 C, for 3 hours. The obtained powder is washed with water and freeze dried to give a fine silica powder with a slight yellow color. --
Line 66, please replace in its entirety the paragraph with the following:
   -- 1.1 g OMC was dissolved in 9.9g methyltriethoxysilane. A similar procedure as described in Example 5 was followed. --

UNITED STATES PATENT AND TRADEMARK OFFICE
CERTIFICATE OF CORRECTION

PATENT NO. : 6,303,149 B1
DATED : April 22, 2002
INVENTOR(S) : Shlomo Magdassi et al.

It is certified that error appears in the above-identified patent and that said Letters Patent is hereby corrected as shown below:

Column 8,
Line 39, please replace in its entirety the paragraph beginning with the following:
  -- 1. A process for preparing sol-gel microcapsules loaded with up to 95% (w/w) functional molecules, comprising the steps of:
    a) emulsifying a nonaqueous, water insoluble solution, comprising sol-gel precursors and the functional molecules to be loaded, in an aqueous solution, under shear forces and with surfactants;
    b) mixing and stirring the emulsion obtained in step (a) with an acidic, neutral or basic aqueous solution to obtain loaded sol-gel microcapsules in suspension. --

Column 9,
Line 17, please replace in its entirety the paragraph beginning with the following:
  -- 10. A process according to claim 1 wherein the sol-gel precursors are silicon alkoxide monomers, or silicon ester monomers, of the formula Si(R) (P), where R is a hydroyzable substituent, n is an integer from 2 to 4 P is a non polymerizable substituent and m is an integer from 0 to 4, or a partially hydrolyzed and partially condensed polymer thereof, or any mixture thereof. --
Line 24, please replace in its entirety the paragraph beginning with the following:
  -- 11. A process according to claim 1 wherein the sol-gel presursors are titanium alkoxide monomers, or titanium ester monomers, or monomers of the formula Ti(R) (P), where R is a hydrolyzable substituent, n is an integer from 2 to 6, P is a non polymerizable substituent and m is an integer from 0 to 6, or a partially hydrolyzed and partially condensed polymer thereof, or any mixture thereof. --
Line 31, please replace in its entirety the paragraph beginning with the following:
  -- 12. A process according to claim 1 wherein the sol-gel precursors are zinc or zirconium alkoxide monomers, or zinc or zirconium ester monomers, or monomers of the formula Zn(R) (P) or Zr(R) (P), where R is a hydrolyzable substituent, n is an interger from 2 to 6, P is a non polymerizable substituent and m is an integer from 0 to 6, or a partially hydrolyzed and partially condensed polymer thereof, or any mixture thereof. --

UNITED STATES PATENT AND TRADEMARK OFFICE
CERTIFICATE OF CORRECTION

PATENT NO.    : 6,303,149 B1
DATED         : April 22, 2002
INVENTOR(S)   : Shlomo Magdassi et al.

It is certified that error appears in the above-identified patent and that said Letters Patent is hereby corrected as shown below:

<u>Column 10,</u>
Line 21, please replace in its entirety the paragraph beginning with the following:
   -- 17. A process according to claim 1 wherein the functional molecules or substances are selected from the group consisting of fragrances, perfumes, colors and dyes, food colors and food additives, antioxidants, humidifiers, vitamins, explosives, insecticides, herbicides and fungicides, or biological molecules selected from the group consisting of enzymer and anitbodies, and drugs, catalysts and reagents. --

Signed and Sealed this

Eighth Day of October, 2002

*Attest:*

*Attesting Officer*

JAMES E. ROGAN
*Director of the United States Patent and Trademark Office*